(12) United States Patent
Rudd et al.

(10) Patent No.: US 8,182,496 B2
(45) Date of Patent: May 22, 2012

(54) DEGRADABLE COMPOSITE MATERIAL WITH FIBRES HAVING VARIOUS DEGRADATION RATES

(75) Inventors: Christopher Douglas Rudd, Nottingham (GB); Andrew James Parsons, Nottingham (GB); Gavin Stuart Walker, Nottingham (GB)

(73) Assignee: University of Nottingham (GB)

( * ) Notice: Subject to any disclaimer, the term of this patent is extended or adjusted under 35 U.S.C. 154(b) by 133 days.

(21) Appl. No.: 12/442,466

(22) PCT Filed: Sep. 21, 2007

(86) PCT No.: PCT/GB2007/003583
§ 371 (c)(1),
(2), (4) Date: Nov. 5, 2009

(87) PCT Pub. No.: WO2008/035088
PCT Pub. Date: Mar. 27, 2008

(65) Prior Publication Data
US 2010/0105799 A1    Apr. 29, 2010

(30) Foreign Application Priority Data
Sep. 23, 2006  (GB) .................................. 0618787.6

(51) Int. Cl.
*A61L 27/10* (2006.01)
*A61L 27/54* (2006.01)

(52) U.S. Cl. ........................................ 606/151; 428/325

(58) Field of Classification Search ............... 623/23.75; 606/151; 428/325
See application file for complete search history.

(56) References Cited

U.S. PATENT DOCUMENTS

| | | | |
|---|---|---|---|
| 4,512,038 A * | 4/1985 | Alexander et al. | 623/23.75 |
| 4,655,777 A * | 4/1987 | Dunn et al. | 424/423 |
| 6,113,640 A * | 9/2000 | Tormala et al. | 623/18.11 |
| 6,682,673 B1 * | 1/2004 | Skwiercz et al. | 264/128 |
| 6,685,956 B2 * | 2/2004 | Chu et al. | 424/423 |
| 6,689,374 B2 * | 2/2004 | Chu et al. | 424/423 |
| 6,790,455 B2 * | 9/2004 | Chu et al. | 424/423 |
| 6,923,811 B1 * | 8/2005 | Carl et al. | 623/17.11 |
| 7,172,765 B2 * | 2/2007 | Chu et al. | 424/423 |
| 7,323,190 B2 * | 1/2008 | Chu et al. | 424/426 |
| 2002/0173213 A1 * | 11/2002 | Chu et al. | 442/414 |
| 2003/0054035 A1 * | 3/2003 | Chu et al. | 424/486 |

(Continued)

FOREIGN PATENT DOCUMENTS

EP    687711 A2 * 12/1995

(Continued)

OTHER PUBLICATIONS

Jiang, A, et al., "Preparation of Poly(ε-caprolactone)/Continuous Bioglass Fibre Composite Using Monomer Transfer Moulding for Bone Implant," Biomaterials 26(15):2281-2288, May 2005.

*Primary Examiner* — James J Seidleck
*Assistant Examiner* — Peter A Salamon
(74) *Attorney, Agent, or Firm* — Christensen O'Connor Johnson Kindness PLLC (57) ABSTRACT

A degradable composite comprising a degradable matrix, a first fiber type and a second fiber type, wherein the first fiber type has a different rate of degradation to that of the second fiber type.

11 Claims, 8 Drawing Sheets

U.S. PATENT DOCUMENTS

| | | | |
|---|---|---|---|
| 2003/0075822 A1* | 4/2003 | Slivka et al. | 264/45.3 |
| 2003/0228350 A1* | 12/2003 | Chu et al. | 424/443 |
| 2004/0054372 A1* | 3/2004 | Corden et al. | 606/77 |
| 2004/0059333 A1* | 3/2004 | Carl et al. | 606/61 |
| 2005/0081750 A1* | 4/2005 | Xu et al. | 106/35 |
| 2005/0215672 A1* | 9/2005 | Mohanty et al. | 524/9 |
| 2005/0226904 A1* | 10/2005 | Choi et al. | 424/426 |
| 2005/0240281 A1* | 10/2005 | Slivka et al. | 623/23.75 |
| 2006/0093645 A1 | 5/2006 | Janas | |
| 2006/0147689 A1* | 7/2006 | Wallajapet et al. | 428/292.1 |
| 2006/0178739 A1* | 8/2006 | Shalaby et al. | 623/1.49 |
| 2008/0065123 A1* | 3/2008 | Yli-Urpo et al. | 606/151 |

FOREIGN PATENT DOCUMENTS

| | | | |
|---|---|---|---|
| EP | 1405647 A1 * | 4/2004 | |
| EP | 1611906 A1 * | 1/2006 | |
| WO | 98/56317 A1 | 12/1998 | |
| WO | WO 9856317 A1 * | 12/1998 | |
| WO | WO 9911297 A2 * | 3/1999 | |
| WO | 2005/005609 A2 | 1/2005 | |
| WO | WO 2005005609 A2 * | 1/2005 | |

* cited by examiner

DEGRADABLE COMPOSITE MATERIAL WITH FIBRES HAVING VARIOUS DEGRADATION RATES

The present invention relates to degradable composites and their use. In particular, the invention relates to degradable composites suitable for use in medical implants.

Many different composites have been used to produce medical implants. Known composites include synthetic permanent composites, made of materials such as acrylic polymer, silicone elastomer, ceramic polymer, polymethylmethacrylate, polyethylene and porous PTFE-carbon fibre. Such composites have been used to produce permanent implants used in the reconstruction of traumatic, developmental and surgical osseous defects. A disadvantage of many of these permanent implants is that the composites lack the strength conferred by bone. Also, as the composites are permanent, they are never replaced by natural bone. Thus if permanent composites are used in a child they will have to be replaced as the child grows.

As well as permanent composites, attempts have been made to develop biodegradable composites for use in producing medical implants. Examples of such biodegradable composites include bioceramics of calcium phosphate such as biodegradable tricalcium phosphate and hydroxyapatite products. Bioceramics, whilst being biocompatible and biodegradable, do not appear to induce pronounced osteogenesis. Furthermore, the inherent hardness of bioceramics makes them difficult to shape. The implants are also rigid when implanted, which can place unwanted stresses around the implant site.

Another approach to produce medical implants has been to use collagen/ceramic/marrow mixes. Such mixtures are only available as a paste-like mix, thus have limited use, for example in fracture repair.

An aim of the present invention is to provide an improved degradable composite material with tailored biodegradation and mechanical properties. Preferably the composite is biodegradable.

According to a first aspect, the invention provides a degradable composite comprising a degradable matrix, a first fibre type and a second fibre type, wherein the first fibre type has a different rate of degradation to the second fibre type.

The rate of degradation of the fibre and/or the matrix can be determined by using a method similar to that of Rinehart et al in Journal of Biomedical Materials Research Part B, 1999, Vol 48, Pgs 833-840.

The degradation rate of the fibre and/or matrix is preferably determined under physiological conditions, that is, the rate that the fibre or matrix would degrade when implanted in a human or animal body.

Some or all of the fibres and/or the matrix may be biodegradable.

The fibres may have a ratio of length to diameter of from about 10:1 to about 20,000:1. The fibres may have a diameter of from about 1 micron to about 5 mm, preferably the fibres have a diameter of from about 10 to 500 microns, more preferably from about 10 to about 300 microns, more preferably from about 100 microns to about 300 microns.

The fibres of the first and/or the second fibre type may be all of the same size, that is, of the same length and/or diameter. Alternatively, the composite may comprise fibres of the first and/or second fibre type that are of more than one size, that is, are of more than one length and/or diameter.

The composite may comprise fibres that are as long as the longest length of the composite. The composite may additionally or alternatively comprise fibres that are shorter then the longest length of the composite.

At least one of the first or second fibre types may have a degradation rate which is faster than that of the matrix. Alternatively, both the first and second fibre types may have faster rates of degradation than the matrix. In a further embodiment, the matrix may have a faster rate of degradation than either the first or second fibre type or both.

The composite may contain more than one fibre of the first fibre type and/or more than one fibre of the second fibre type. The composite may comprise at least about 10 fibres of the first fibre type and at least about 10 fibres of the second fibre type. The composite may comprise hundreds, thousands or tens of thousand of fibres of the first and/or second fibre type.

The composite may comprise between about 1% and about 90% volume fraction of fibre. The composite may comprise between about 10% and about 75% volume fraction of fibre. The composite may comprise between about 20% and about 60% volume fraction of fibre. The composite may comprise between about 10% and about 40% volume fraction of fibre.

Up to about 99% of the fibres in the composite may be of the first fibre type. Up to about 99% of the fibres in the composite may be fibres of the second fibre type. Up to about 70% of the fibres in the composite may be of the first fibre type, and up to about 70% of the fibres in the composite may be fibres of the second fibre type. About 50% of the fibres in the composite may be fibres of the first type and about 50% of the fibres in the composite may be fibres of the second type.

In addition to fibres of the first and second fibre type the composite may comprise additional fibres of one or more different types. The composite may comprise three, four, five, six or more different fibre types. The composite may comprise more than ten different fibre types. The additional fibre types may have a rate of degradation which is different to, or the same as, the rate of degradation as fibres of the first and/or second fibre type and/or the matrix.

Fibres of the first and/or second fibre type may serve as reinforcing fibres. Alternatively, or additionally, the composite may also comprise additional reinforcing fibres. The reinforcing fibres may improve the final strength of the composite. The reinforcing fibres may be fibres of the first or second fibre type, or they may be fibres of a different type.

Fibres of the first fibre type and fibres of the second fibre type may be of a different chemical composition.

Fibres of the first and second fibre type may both be derived from the same chemical composition. Fibres of the first and second fibre type may both be derived from fibres of the same chemical composition.

Fibres of the first fibre type and fibres of the second fibre type may have the same chemical composition, but one or both of the fibre types may have been treated such that fibres of each type have altered degradation properties. The treatment to alter the degradation properties may not alter the chemical composition of the treated fibre when compared to untreated fibre. The fact that the treated fibres have a different rate of degradation is sufficient to distinguish the fibres into first and second fibre types.

Treatment of one or more fibres of the first or second fibre type to alter the degradation properties may alter the chemical composition of the treated fibre when compared to untreated fibre.

Preferably the first and/or second fibre type is treated to alter the degradation rate of the fibre after the fibre has been drawn.

Fibres for use in the invention may be drawn using any suitable method; this may include processes similar to those used in glass fibre production. The material to be drawn may first be melted. The material may be melted in a crucible. The crucible may be made of platinum. The melted material may then be allowed to pass through one or more ports or holes in the base of the crucible (such a hole is generally referred to in the industry as a bushing). The material may then be drawn onto a bobbin or spool or similar, which may attenuate the fibre to the correct diameter. The fibre may then be cooled.

Fibres for use in the invention may be chemically and/or thermally and/or mechanically treated to alter the rate at which they degrade. Preferably the fibres to be treated are treated after they have been drawn. In one embodiment, fibres are drawn and then thermally treated, that is, they are subjected to a post drawing heating or annealing process in order to alter the degradation properties of the fibres. The rate of degradation and/or the mode of degradation may be altered.

Annealing is a method of heat-treating a fibre by which the fibre is heated to a point below its glass transition temperature (Tg). This method may allow stresses to be removed from the material. The loss of stresses occurs at a different rate depending on the temperature at which the material is held. The optimum temperature to anneal a fibre, and in particular a glass fibre, is at its 'annealing point', which is slightly below the Tg of the fibre, at a specific viscosity of $10^{13}$ poise. (http://www.cmog.org/index.asp?pageId=744). However, annealing can occur at lower temperatures, just more slowly.

The fibres may be heat treated/annealed, by heating the fibres at a temperature of between about 1° C. and about 20° C. below the glass transition temperature of the fibres. Preferably, the fibres are heated at a temperature of between about 1° C. and about 10° C., preferably about 5° C., below the glass transition temperature of the fibres. Preferably the fibres are heated treated for from about 30 seconds to about 12 hours. More preferably the fibres are heat treated from about 1 minute to about 3 hours, preferably about 90 minutes or less.

Once the fibres have been annealed, residual stresses in the fibres may be reduced, this may reduce stress corrosion of the fibre surface which may result in a loss of strength.

The fibres may be chemically treated with a sizing agent, this may make the glass surface more organophilic and more easily able to bond with a polymer matrix.

The fibres may also be treated with a film former, this may be used to bind the fibres together into tows.

Fibres may be chemically treated by the application of a lubricant, this may be applied to protect the fibre from damage and/or to make handling easier.

The fibre surface may be etched to roughen it.

The fibre may be hydrothermally treated to alter properties of the surface of the fibre, for example, to promote hydroxy groups on the surface; this may make the application of a sizing agent easier.

A coupling agent and/or sizing agent may be applied to the surface of the fibres. The agent may be applied to some or all of the fibres used in the composite.

A coupling agent and/or a sizing agent may be applied to only the first or second fibre type, the first and second fibre types may have the same or a different chemical composition.

A coupling agent may be added to improve adhesion between fibre and matrix. An example of a coupling agent is 3-aminopropyl triethoxy silane. 3-aminopropyl triethoxy silane bonds to the surface of a fibre, such as a glass fibre, making it more organophilic, so that the fibre will bond more effectively with a polymer matrix.

All of, or just a portion of, a fibre surface may be treated.

By mechanically and/or thermally and/or chemically treating drawn fibres the degradation properties of the fibres can be adjusted and controlled.

In one embodiment of the invention, the first fibre type is derived from a fibre of the same chemical composition as the second fibre type, but the first fibre type has been thermally treated/annealed to alter the degradation properties of the first fibre type compared to the second fibre type. Preferably the chemical composition of the first and second fibres is the same.

The advantage of using first and second fibre types where the fibres are of the same chemical composition, but have been treated differently to give them different degradation rates, is that only one fibre drawing facility is needed. This results in a dramatic cost saving over using two different types of fibres, with different chemical compositions, which would require two fibre-drawing facilities.

The first and/or second fibre types could be synthetic and/or natural fibres. The first and/or second fibre types may be selected from the group comprising natural fibres, ceramic fibres, carbon fibres, glass fibres, Bioglass® fibres, silica based bioactive glasses, fibres made from silica mixtures, aramide fibres, polyethylene fibres, polyamide fibres, lactide fibres, glycolide fibres, caprolactone fibres and the like, or copolymers and/or mixtures thereof. Natural fibres may be flax, jute or hemp.

Preferably the first and/or second fibre types are phosphate glass fibres. Preferably both the first and second fibre types are phosphate glass fibres.

Glass formulations used to make fibres for use in the invention may include any of, or mixtures of, phosphate, calcium, sodium, magnesium, zinc or iron. For example, phosphate glass is a glass in which phosphate is the primary network former. Phosphate glass fibres may be fibres of $P_{40}Na_{20}Ca_{16}Mg_{24}$. The first and second fibre types may be different glass fibres, that is, with different chemical compositions; or they may be glass fibres with the same chemical composition, but where one or both fibre types have been treated to alter their degradation properties.

In one embodiment, the first and second fibre types are both phosphate glass fibres of the same chemical composition, but one fibre type has been treated, for example thermally, mechanically and/or chemically, to alter its rate of degradation compared to untreated fibres. Preferably one fibre type has been heat treated/annealed to alter the rate of degradation.

In another embodiment the first and second fibre types are both derived from phosphate glass fibres of the same chemical composition, but thermal, chemical or mechanical treatment of the first and/or second fibre type has altered the chemical composition of the fibre type, as well as the rate of degradation of the fibre type.

The degradation rates of phosphate glass fibres which may be used in the invention may range from about $0.1$ $gcm^{-2}$ $hr^{-1}$ to about $10^{-8}$ $gcm^{-2}$ $hr^{-1}$, depending on their composition. The phosphate glass fibres may have a degradation rate in the region of about $10^{-6}/10^{-7}$ $gcm^{-2}$ $hr^{-1}$.

The fibres may be in any form, length or diameter or mixtures thereof and arranged in any orientation or orientations, with or without directional bias. The fibres may be loose, aligned, knitted or woven. The length and orientation of the fibres may be selected to confer desired mechanical properties and/or a specific degradation profile on the composite.

Composites may comprise long woven fibres. The fibres may be provided as layers of different types of fibre, such as different types of glass fibres. Alternatively, different types of fibre, such as different types of glass fibres, may be used in the same weave. Different types of fibre may include fibres of the same chemical composition which have been treated to alter their rate of degradation.

By controlling the matrix and fibre types used in the composite, some of the physical and chemical properties of the composite may be controlled. For example, stiffness could be preferentially maintained in one direction or area, such as at a fixation point, of the composite by controlling what the fibres are and where they are.

The fibres may be arranged in the composite in order to impart anisotropic properties to the composite The fibres may be arranged in the composite to provide areas which are stronger than others, or areas where the fibres will degrade more rapidly to produce a more porous area.

By using fibres with different degradation rates the properties of composites can be tailored to allow tissue reconstruction to be maximised. The composite of the present invention offers the means to produce precise three-dimensional composite structures for surgical implants.

By tailoring the degradation rates, composites can be designed to suit specific tissue growth characteristics. For example, by tailoring degradation rates in the composite, differential degradation of the composite can be effected, allowing an intermediate porous scaffold structure to form once the composite has been implanted. Mechanical properties of the composite can also be controlled to suit the loading conditions of the implant by controlling degradation in the composite.

The matrix in the composite may be made of a material selected from the group comprising acrylics, polyesters, polyolefins, polyurethanes, silicon polymers, vinyl polymers, halogenated hydrocarbons such as Teflon', nylons, proteinaceous materials, and copolymers or combinations thereof. For example, the matrix may be a polyorthoester made from polylactides, poly lactic acids (PLA, PLLA, PDLLA), epsilon caprolactone, polycaprolactone (PCL), polyglycolic acid (PGA), polypropylene fumarate, polycarbonates such as polymethyl carbonate and polytrimethylenecarbonate, polyiminocarbonate, polyhydroxybutyrate, polyhydroxyvalerate, polyoxalates such as poly(alkylene)oxalates, polyamides such as polyesteramide and polyanhydrides, and copolymers and combinations thereof. In particular, poly (DL-lactide-co-glycolide) (DL-PLG), poly (L-lactide-co-glycolide), copolymers of polyhydroxybutyrate and polyhydroxyvalerate.

Preferably the matrix is selected from polymers and copolymers of aliphatic polyesters, such as poly-ε-caprolactone and/or biocompatible derivatives and analogues thereof.

Preferably the matrix is a thermoplastic polymer.

Preferably the matrix is biodegradable.

Preferably the entire composite is biodegradable. The composite may degrade, in use, in between about 2 hours and about 6 years. Different components of the matrix may degrade at different rates. For example, whilst the matrix may be made of poly lactic acid, which takes from about 3 to about 5 years to be fully degraded when implanted in a human or non-human animal, some fibres within the composite may degrade much quicker. For example, some fibres in the composite may degrade in between about 2 hours and less than about 2 years when implanted in a human or non-human animal. This differential degradation may allow the composite to develop pores or channels within the composite which allow the composite to serve as a scaffold. The porous scaffold may allow cells to adhere to it, or nutrients to pass through it, or agents to be released from the remaining composite. Where the composite is intended for use as a medical implant it may be necessary to ensure rapid and extensive vascularisation of the implant to ensure that cells can colonise and eventually replace the implant.

Preferably the composite is bio-resorbable as well as biodegradable, that is, once the composite has degraded the body can resorb it.

Preferably one or more of the fibres in the composite is arranged to degrade, in use, faster than the matrix. This may allow pores or channels to be formed in the composite. Cells, such as osteoblasts, may then infiltrate into the composite and allow tissue, such as bone, formation to begin. Tissue may eventually replace the composite once it has degraded. By controlling the fibre types used the, rate of degradation of the fibres, and the location of the fibres, the pattern of degradation of the composite may be controlled and thus the porosity of the composite in use may be controlled and tailored to a particular environment and use. For example, specific cells may only, or may more efficiently, colonise pores of a specific size. Preferably the composite is designed for primary growth of cells selected from bone, cartilage, tissue and the like. The degradation of the fibres and matrix is preferably tailored to create a support structure for live bone or cartilage cells, or live vascular cells, within the partially degraded composite.

The ability to control and vary the degradation properties in a composite is extremely desirable, in particular in biodegradable composites for use in medicine. In particular the anisotropic control of properties is particularly interesting, and allows control of degradation in different areas of the composite, which may help to maintain properties around key areas such as fixation points, or sides of the composite that experience, for example, greater bending stresses.

The composite may initially be dense. Preferably the composite is non-porous. However, in use, when degradation of the composite occurs the composite may become porous and less dense.

Preferably the composite is not initially a tissue scaffold. However, a tissue scaffold may form when the composite is implanted and partial degradation occurs.

Preferably the composite is a polyester matrix with phosphate glass fibres. Preferably a portion of the phosphate glass fibres are thermally treated/annealed after being drawn, and a portion are not, such that the thermally treated/annealed fibres (fibres of a first type) and the non-annealed fibres (fibres of a second type) have different rates of degradation. The polyester matrix is preferably poly-ε-caprolactone.

The composite may be produced by any standard method of composite production, such as compression moulding, resin injection or monomer transfer moulding. Preferably, monomer transfer moulding is used to produce the composite. Monomer transfer moulding may comprise placing at least the first and second fibre types into a sealed mould. The fibres are placed in the mould in the desired orientation to produce a composite with desired properties. The fibres, when placed in a desired shape and orientation, may be referred to as a shaped preform. A reacting mixture of monomer is then introduced into the mould containing the fibres. Polymerisation of the monomer in the mould may be achieved by any suitable means, for example, by heating or by the addition of an initiator or a catalyst. In one embodiment, where polymerisation is achieved through heat, the mould is maintained at a set temperature for sufficient time for the polymerisation of the monomer to proceed. Once the monomer has polymerised, forming the matrix, the mould is then rapidly quenched to room temperature and the composite is de-moulded. This method is described in detail in European Patent No: 1 005 379.

Catalysts which may be used in monomer transfer moulding include, but are not limited to, diethyl zinc, stannous octoate boron trifluoride and mixtures thereof.

Preferably composites according to the invention are made by in situ processing of a thermoplastic matrix precursor in a shaped preform of fibres, wherein the fibres include two or more fibre types each with different rates of degradation.

A shaped preform of fibres may be any presentation of fibres in a suitable tool, mould or the like adapted for impregnation with polymer or polymer precursors to provide a composite. The shaped fibre preform preferably enables a predetermined regular, irregular or otherwise profiled fibre distribution.

The composite may be used anywhere in which a degradable composite could be utilised. The composite is particularly suited to medical applications, and in particular to the repair of damaged or defective hard tissue. It also has potential application to any orthopaedic areas, in particular in areas of low-loading, for example, maxillofacial reconstructive surgery, such as orbital floor replacement. The composite may be used in implants for use in fracture fixation. The composite may be used to replace metallic equivalents and offers several advantages over these materials, for example, stiffness matching, colour matching, ease of shaping and contouring (even in theatre), non-magnetic, no temperature related discomfort and no x-ray artefact creation.

The composite may be used in cosmetic or aesthetic surgery.

A composite according to the invention may be a three-dimensional structure such as a pin, plate or custom shaped implants. Alternatively, the composition may be a flat, textile like material. A three-dimensional structure made from the composite may be used in osteosynthesis.

Composites according to the invention may be used in transplant surgery, bone resurfacing or the fixation of fractures and/or tissue scaffolding.

Composites according to the invention may be used in cranio-facial or maxillo-facial surgery, or in orthopaedic surgery such as the replacement of bone, cartilage and/or meniscus.

Composites according to the invention may be moulded to any size or shape that is desired.

Custom made implants with predetermined shape, physical properties and degradation profile may be made from composites according to the invention. This is particularly advantageous in implant/reconstructive surgery where no two implants are identical.

The composite may be coated with, or associated with, or have embedded therein, or be impregnated with, an appropriate therapeutic agent. Preferably the therapeutic agent is one or more of an antibiotic, a growth promoter and a vitamin supplement.

The composite may be coated with, or associated with, or have embedded therein, or be impregnated with, a population of host and/or compatible cells. Preferably the cells are derived from one or more of bone, cartilage, collagen or vascular tissue. The selection of cells will depend on the intended site of implantation of the composite.

It will be appreciated that given the relative rigidity and impact resistance of the composite, and its ability to be degradable, the composite may also have applications in the fields of consumer goods, packaging, storage and transport aids.

According to another aspect, the invention provides a biodegradable composite comprising a biodegradable polymer matrix containing fibres of a first and fibres of a second fibre type, wherein the fibres of the first and second fibre types have the same chemical composition, or are derived from fibres with the same chemical composition, but have different rates of degradation.

Preferably fibres of the first and/or second fibre type have been treated to alter the rate of degradation of the fibres. Preferably fibres of the first and/or second fibre type were treated after they were drawn.

Preferably the first and second fibre types are phosphate glass fibres. Preferably fibres of the first or second fibre type have been thermally treated/annealed after being drawn to alter the degradation behaviour/profile of the fibres. Preferably the fibres of the first and second fibre type have the same chemical composition and differ in that one has been thermally treated/annealed post-drawing to alter the rate of degradation.

According to a further aspect, the invention provides a process for producing a degradable composite comprising:
providing a shaped preform of fibres in a tool or a mould, wherein the preform contains fibres of a first fibre type and fibres of a second fibre type, wherein the first and second fibre types have different rates of degradation;
injecting into the tool or mould containing the fibre preform a composition comprising monomers and/or co-monomers and/or oligomers and/or resin; and
polymerising the monomers and/or co-monomers and/or oligomers and/or resin to form a composite.

Preferably the composition is injected in such a manner as to retain the distribution, orientation and/or shape of the fibres in the mould or tool.

Preferably, the monomers and/or co-monomers and/or oligomers and/or resin are polymerised either by the application of heat and/or by the addition of a catalyst and/or initiator.

The process allows the production of a shaped composite, according to any preceding aspect of the invention, with controlled degradation and/or mechanical properties.

The skilled man will appreciate that all the preferred features of the invention relating to the composite of the invention can be applied to composites produced using the process of the invention.

The skilled man will also appreciate that all the preferred features of the invention relating to the first described aspect of the invention can be applied to all composites of the invention.

According to another aspect, the invention provides a composite produced by the process of the invention.

According to a further aspect, the invention provides the use of a composite according to any aspect of the invention in the production of a medical implant.

Preferably the medical implant is for use in cranio-facial or maxillo-facial surgery, or for orthopaedic surgery.

Preferred embodiments of the invention will now be described, merely by way of example, with reference to the following figures and examples.

COMPOSITE FABRICATION EXAMPLE

All chemicals unless stated otherwise were obtained from Sigma Aldrich and used as received.

Annealing of Phosphate Glass Fibres $P_{40}Na_{20}Ca_{16}Mg_{24}$ phosphate glass fibres were drawn by gravity feed through a bushing and onto a bobbin. The diameter of the fibres produced ranged from 15-25 microns.

Small batches of fibres (a few grams) were then annealed (thermally treated post-drawing) by undergoing heat treatment for 90 minutes at 5° C. below the glass transition temperature ($T_g$) of the glass. The small batches of fibres were enclosed in a glass container (Pyrex®) and slowly heated (1° C./min) to temperature. They were then maintained at the chosen temperature and then cooled again very slowly back down to room temperature (0.25° C./min)

Sizing of Phosphate Glass Fibres

Phosphate glass fibres (annealed or non-annealed) were sized by treatment with 3-aminopropyl triethoxy silane. The silane was made up as a 1% v/v solution in a mixture of 90% ethanol and 10% distilled water. 1.5 g of phosphate glass fibres were immersed in 100 ml of the silane solution for 15 minutes, before being vacuum filtered and washed with 50 ml of ethanol. The fibres were then dried for 24 hours at 120° C.

The fibres were sized using silane to make the glass surface organophilic and thus more compatible with the polymer matrix, resulting in a better adhesion between fibre and matrix.

Composite Manufacture

A 25% volume fraction of fibre, annealed or non-annealed or a mixture thereof, was introduced into a mould of dimensions 84 mm×30 mm×2 mm. Bundles/tows of the fibre were cut to the correct length and carefully placed in the mould by hand. The mould was then sealed.

ε-caprolactone monomer was distilled under reduced pressure over fresh calcium hydride. The monomer was then placed into a sealed three necked flask equipped with a stirrer and purged with nitrogen. 0.1 mol % of catalyst (tin(II)$_2$-ethylhexanoate) was introduced to the monomer and stirred for 5 minutes. The mixture was then injected into the sealed mould and placed into an oven at 120° C. for 24 hours to polymerise and form the matrix. The mould was then opened and the composite removed.

Example Data

Fibre Properties

The following table illustrates the difference between the properties of annealed and non-annealed fibres (as produced by the above described method) both before and after degradation in distilled water at 37° C. Around 40 mg of fibre was sealed in a vial of 20 ml of distilled water at 37° C. for the desired time period before being subjected to tensile testing, following the standard BS ISO11566.

| Fibre Type | Immersion time (days) | Tensile Strength (GPa) | Tensile Modulus (GPa) |
|---|---|---|---|
| Non-annealed | 0 | 0.484(0.153) | 44.0(4.8) |
|  | 1 | 0.457(0.097) | 45.4(4.1) |
|  | 3 | 0.367(0.064) | 43.9(5.6) |
| Annealed | 0 | 0.288(0.051) | 52.0(4.7) |
|  | 1 | 0.307(0.073) | 50.4(7.0) |
|  | 3 | 0.459(0.136) | 51.6(4.1) |

The modulus of annealed fibres is seen to be higher than those that are not annealed. The strength is lower initially but recovers to a comparable value within a few days. This difference in properties can be used in composites according to the invention in order to control and tailor the properties of the composite.

Figure 1:
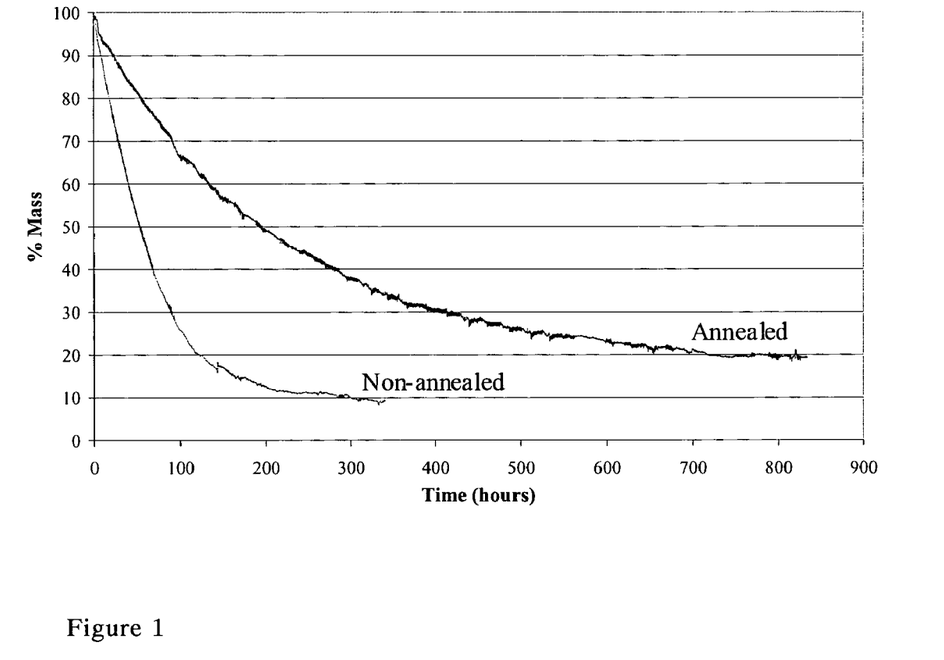
FIG. 1—illustrates weight loss in bundles of annealed and non-annealed glass fibres when immersed in distilled water at 37° C.

FIG. 1 shows the difference in weight loss for bundles of annealed and non-annealed glass fibres immersed in distilled water at 37° C. The bundles contained approximately 100 mg of fibres of around 40 mm in length. They were suspended in a beaker containing 400 ml of distilled water, held at 37° C. The annealed fibres are observed to degrade significantly more slowly.

Figure 2:
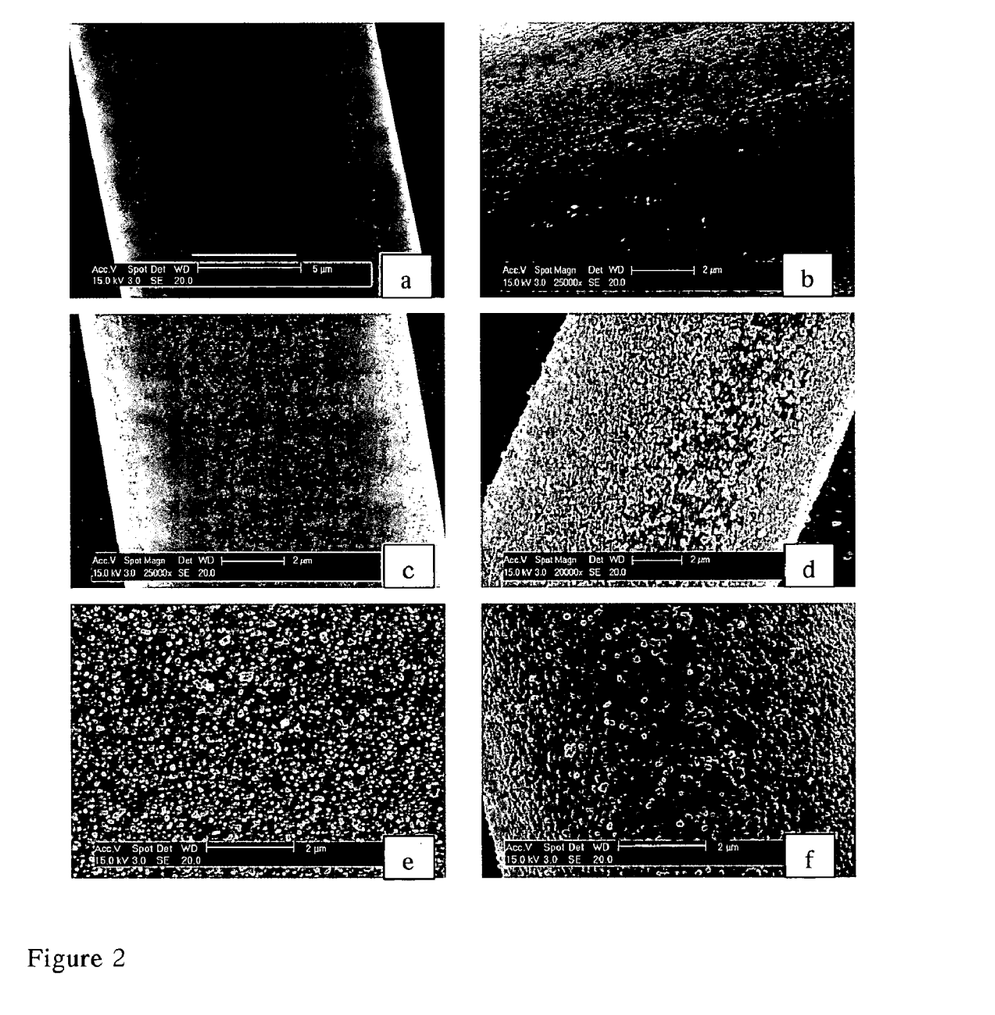
FIG. 2—are scanning electron micrographs (SEMs) of $P_{40}Na_{20}Ca_{16}Mg_{24}$ phosphate glass fibres (a) as prepared, (b) after 1 day in 30 ml distilled water at 37° C. (c) after 3 days in 30 ml distilled water at 37° C., (d) after 1 week in 30 ml distilled water at 37° C., (e) after 2 weeks in 30 ml distilled water at 37° C., and (f) after 6 weeks in 30 ml distilled water at 37° C.
Figure 3:
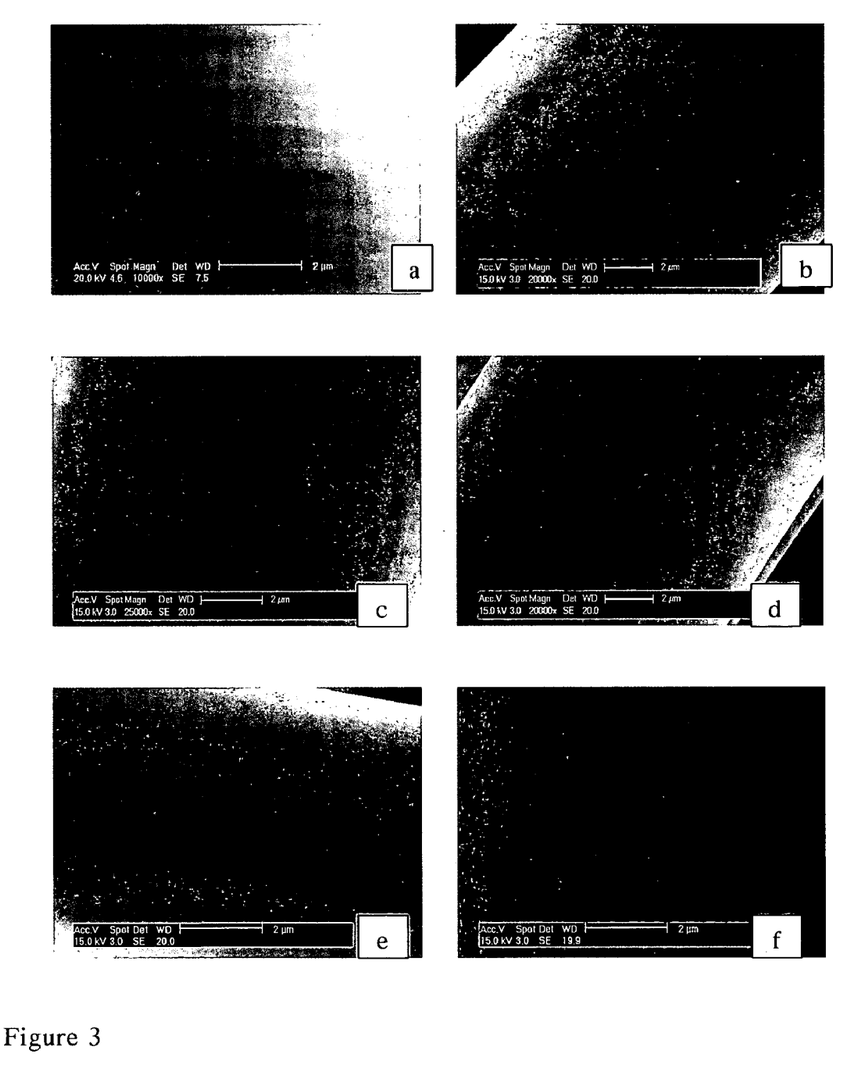
FIG. 3—are SEMs of annealed $P_{40}Na_{20}Ca_{16}Mg_{24}$ phosphate glass fibres (a) as prepared, (b) after 1 day in 30 ml distilled water at 37° C. (c) after 3 days in 30 ml distilled water at 37° C., (d) after 1 week in 30 ml distilled water at 37° C., (e) after 2 weeks in 30 ml distilled water at 37° C., and (f) after 6 weeks in 30 ml distilled water at 37° C.

FIGS. 2 and 3 are scanning electron micrographs (SEMs) of untreated and treated/annealed (respectively) $P_{40}Na_{20}Ca_{16}Mg_{24}$ phosphate glass fibres following 0, 1, 3, 7, 24 and 42 days immersion in distilled water at 37° C. The treated fibres were annealed as described above.

The SEMs show the different modes of degradation in annealed and non-annealed fibres. Non-annealed fibres experience a roughening of the surface, while annealed fibres undergo a steady degradation, leaving a smooth surface.

Composite Properties

The table below illustrates the difference between properties of annealed and non-annealed fibre-containing composites when degraded in distilled water at 37° C. The composites tested were produced using the monomer transfer moulding method described above with unidirectional fibre alignment.

| Composite | Fibre volume fraction | Immersion time (days) | Flexural Strength (GPa) | Flexural Modulus (GPa) |
|---|---|---|---|---|
| Non-annealed | 40 | 0 | 179.9(27.7) | 14.1(0.6) |
|  | 40 | 7 | 27.9(4.8) | 2.1(0.4) |
| Annealed | 40 | 0 | 191.5(17.3) | 19.1(4.4) |
|  | 40 | 7 | 62.5(6.8) | 5.7(1.3) |

The composite samples used were 60×10×2 mm in size and were immersed in 400 ml of distilled water at 37° C. The properties were obtained by performing 3 point bending analysis on the treated composite samples. The values given are an average of five specimens.

The composites containing annealed fibres showed a better retention of properties during degradation in comparison to those with non-annealed fibres.

Figure 4:
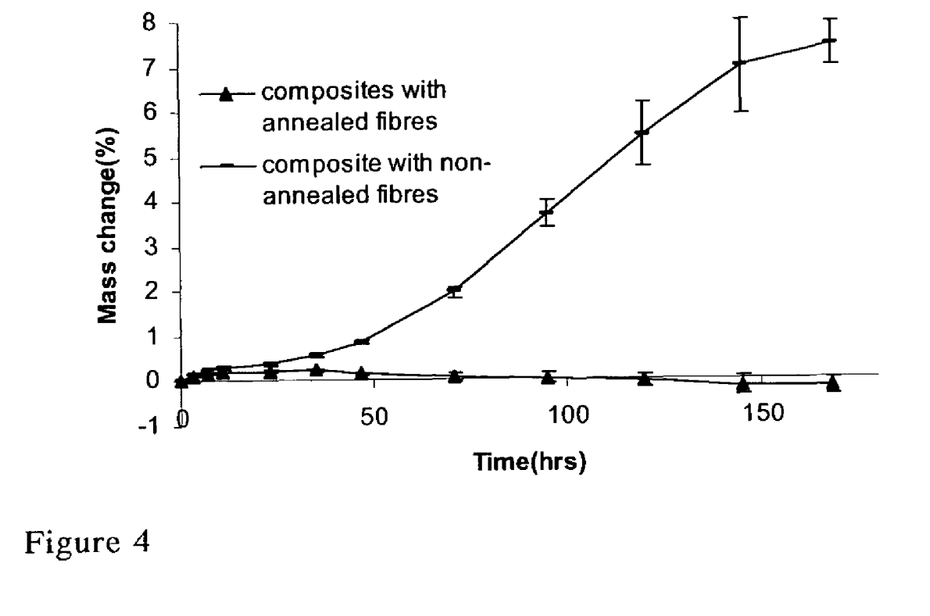
FIG. 4—illustrates the difference in mass gain (water uptake) between composites with annealed fibres and those with non-annealed fibres when immersed in distilled water at 37° C.

FIG. 4 shows the difference in mass gain (through water up-take when immersed in distilled water at 37° C.) between composites with annealed fibres and those with non-annealed fibres. Annealed fibres show very little water uptake, providing much better dimensional stability for the composite.

Figure 5:
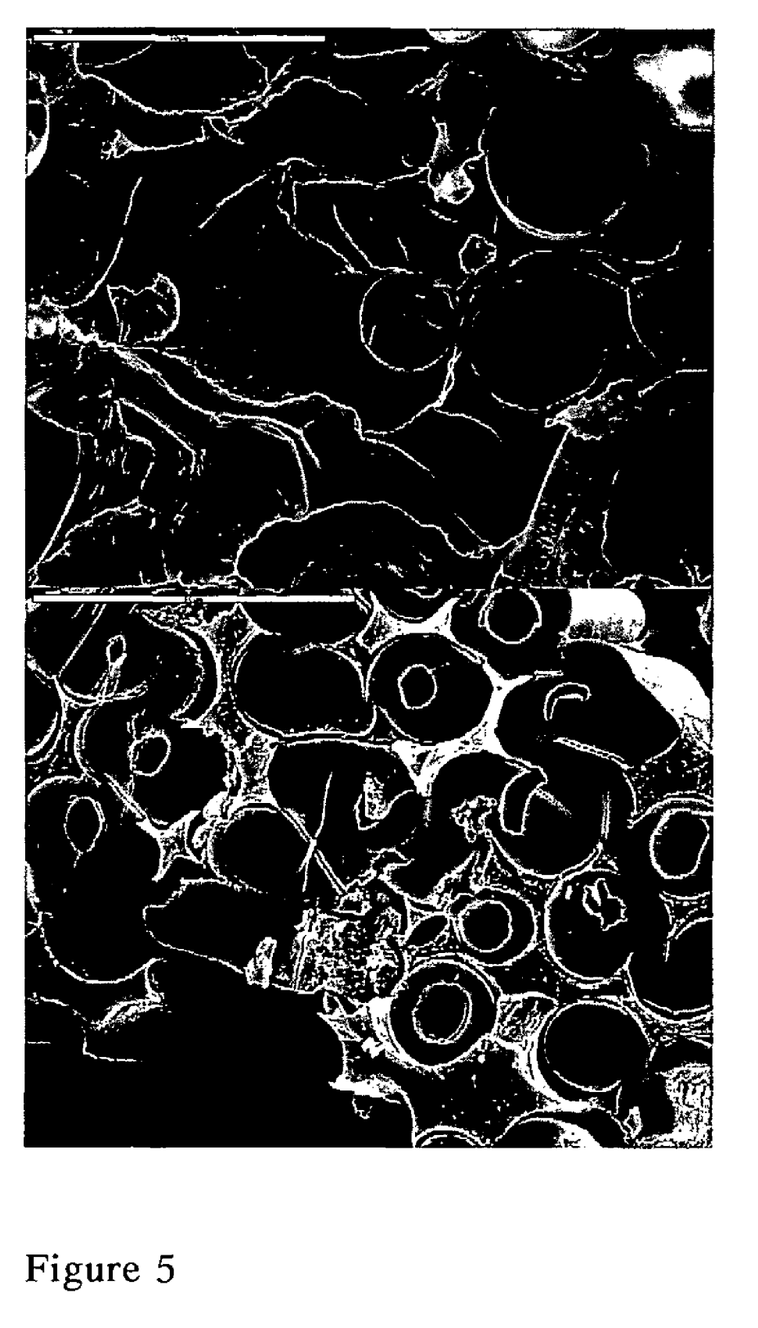
FIG. 5—shows SEMs of the fracture surface of a non-annealed fibre-containing composite. The upper SEM is of the composite as produced and the lower SEM is of the same composite after 1 week degradation in distilled water at 37° C.

FIG. 5 shows SEM pictures of the fracture surface of a non-annealed fibre-containing composite. The upper image shows the composite as produced, the lower image shows the composite after 1 week of degradation in distilled water at 37° C. (lower). The degraded and deformed appearance of the fibres after degradation in water is clearly visible.

Figure 6:
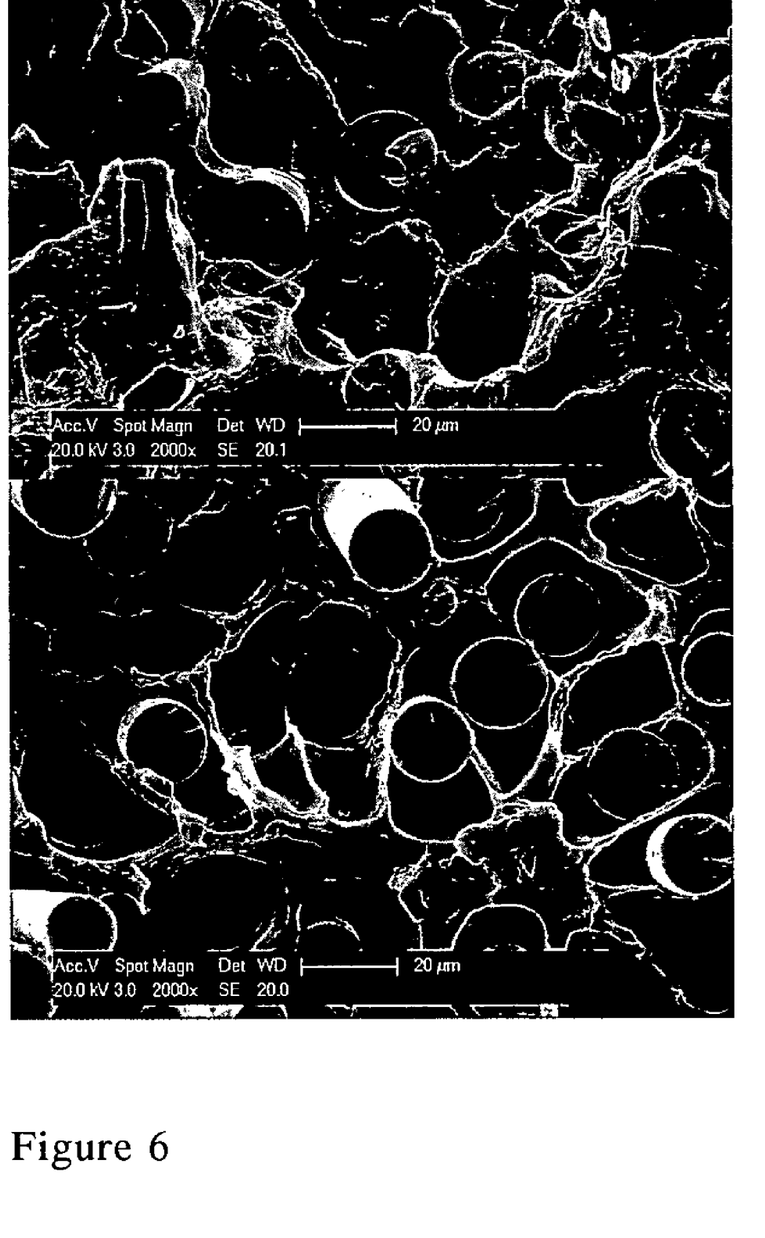
FIG. 6—shows SEMs of the fracture surface of an annealed fibre-containing composite. The upper SEM is of the composite as produced and the lower SEM is of the same composite after 1 week degradation in distilled water at 37° C.

FIG. 6 shows SEM pictures of the fracture surface of annealed fibre-containing composite. The upper image shows the composite as produced, the lower image shows the composite after 1 week of degradation in distilled water at 37° C. (lower). The relatively pristine appearance of the fibres after degradation is clearly visible.

FIGS. 5 and 6 demonstrate that annealed and non-annealed fibres undergo different modes of degradation.

Figure 7:
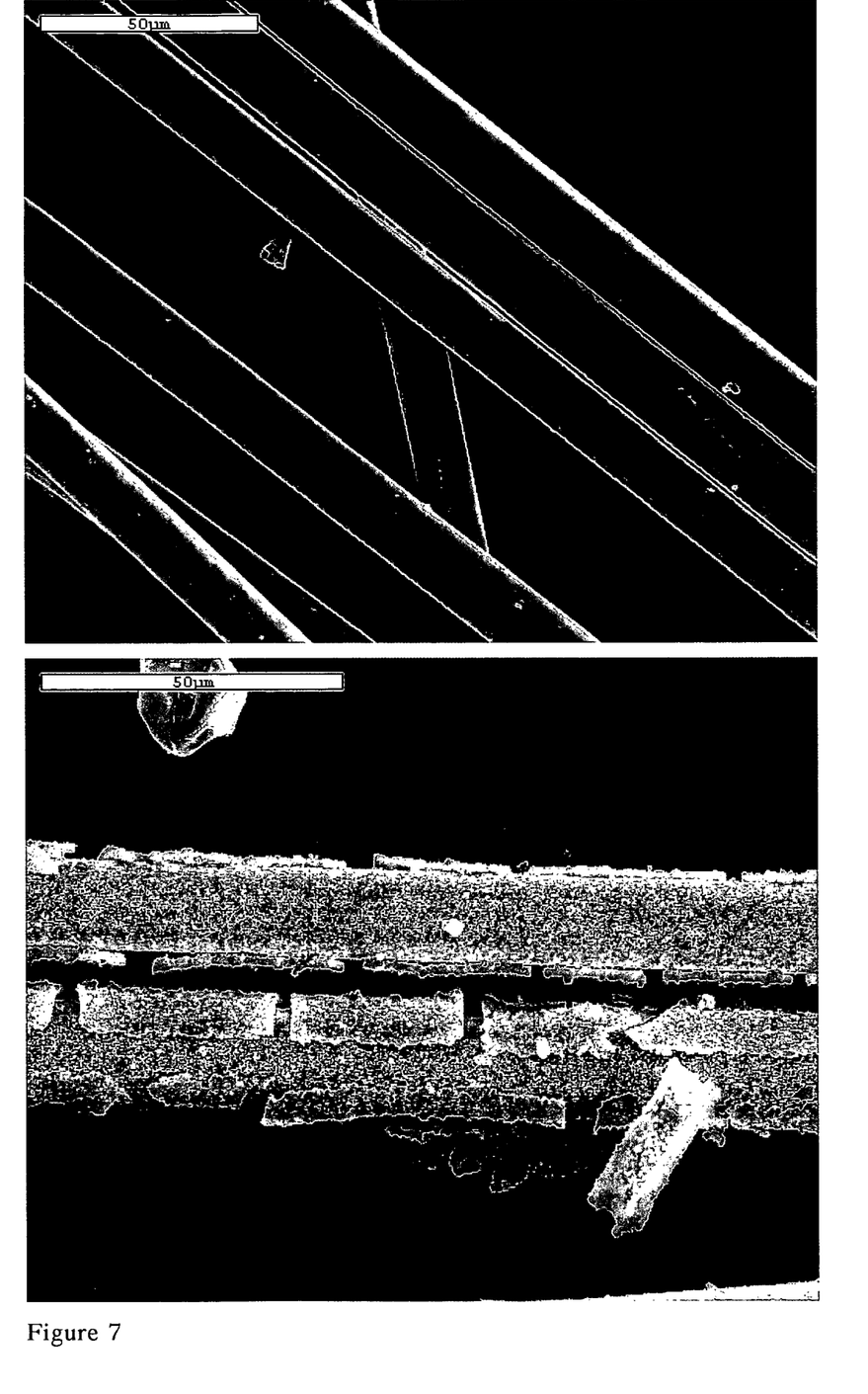
FIG. 7—shows SEMs illustrating the difference in mode of degradation between annealed (upper image) and non-annealed (lower image) phosphate glass fibres after degradation in water at 37° C. for 7 days.
Figure 8:
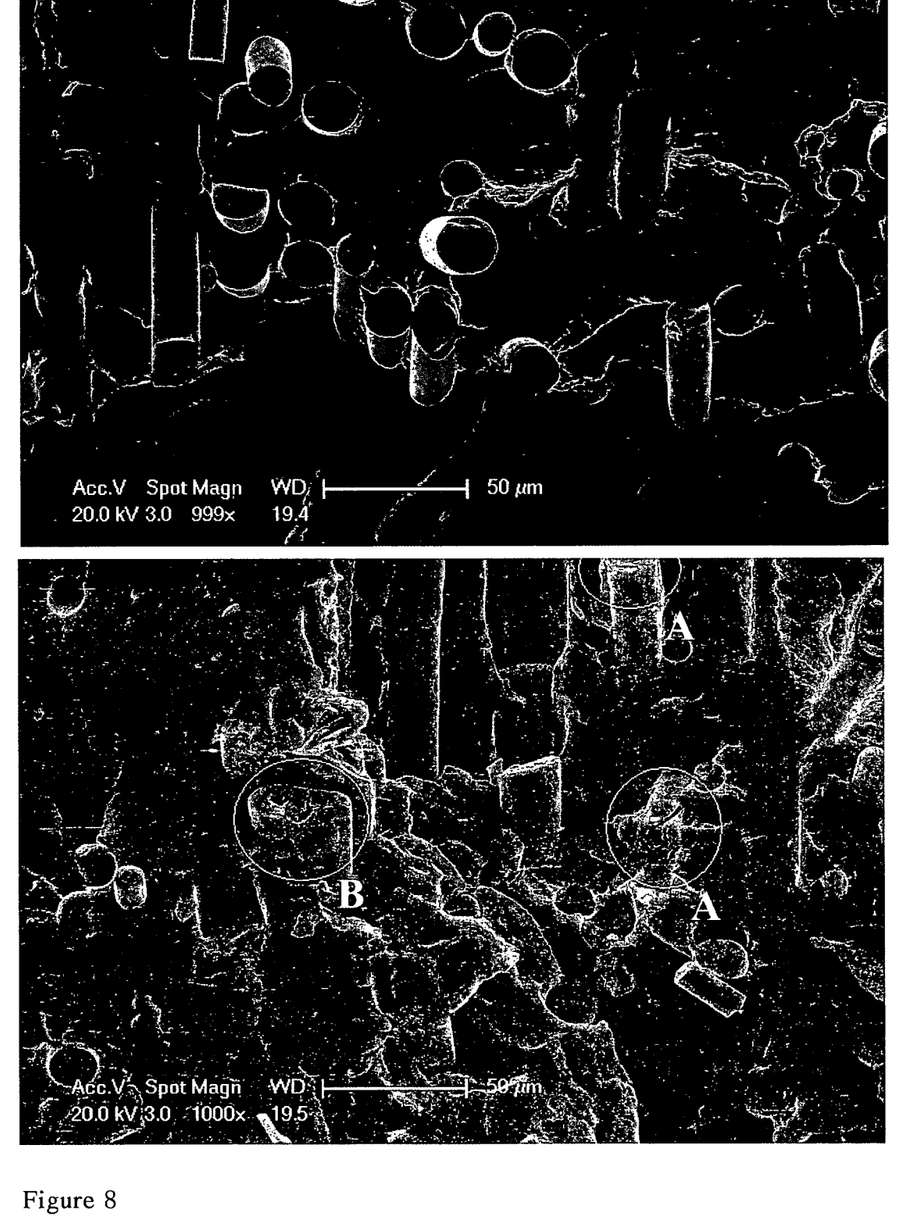
FIG. 8—shows SEMs of different regions of the fracture surface of a mixed fibre composite after degradation in distilled water at 37° C. for seven days. The upper SEM shows annealed fibres and the lower SEM shows non-annealed fibres.

This is further illustrated in FIGS. 7 and 8. FIG. 7 is SEMs illustrating the difference in the mode of degradation between annealed (upper image) and non-annealed (lower image) phosphate glass fibres after degradation in water at 37° C. for 7 days. The annealed glass is seen to degrade in a regular fashion, leaving a smooth surface. The non-annealed glass develops a rough surface as layers of glass peel away from the surface.

FIG. 8 is SEMs of different regions of the fracture surface of a mixed fibre composite. The composite was produced by using compression moulding, with a layer of non-annealed fibre at the base, annealed fibres in the middle and then non-annealed fibre again at the top. The composite was degraded in distilled water at 37° C. for seven days. The annealed fibres (upper image) remain relatively pristine, whilst the non-annealed fibres (lower image) can be seen to crack and lose surface layers (areas marked A) and to begin to deform (area marked B).

The table below shows the difference between interfacial shear strengths for annealed and non-annealed fibres

| Fibre type | Matrix material | IF shear strength (MPa) | Std Deviation |
| --- | --- | --- | --- |
| Non-annealed | PCL | 1.65 | 0.53 |
| Annealed | PCL | 3.37 | 1.24 |

Single phosphate glass fibres were hot-pressed between two thin sheets of polymer to form a single fibre composite. These composites were then put under tensile stress until the fibre breaks, and continues to break until a static value of stress is obtained. The number of breaks observed in the fibre allow the interfacial shear strength to be determined. The quoted values are an average of five specimens.

It can be seen that the annealed fibres exhibit a much-improved interfacial shear strength compared to non-annealed fibres, indicating a better adhesion between fibre and matrix. Better adhesion gives better composite properties. It should also help to maintain the composite/matrix interface and slow down the rate of degradation of composite properties.

The invention claimed is:

1. A degradable composite comprising a degradable matrix, a first fibre type and a second fibre type, wherein the first and second fibre types are phosphate glass fibres, in which phosphate is the primary component, and wherein at least one of the first or second fibre type is thermally treated after being drawn to alter their rates of degradation such that the first fibre type has a different rate of degradation to that of the second fibre type.

2. The composite according to claim 1 wherein the first and second fibre types have the same chemical composition.

3. The composite according to claim 1 wherein the first and second fibre types are derived from fibres of the same chemical composition.

4. The composite according to claim 1 wherein at least one of the first or second fibre type is thermally treated to alter their degradation rates by an annealing treatment.

5. The composite according to claim 1 wherein the matrix is made of a material selected from the group consisting of acrylics, polyesters, polyolefins, polyurethanes, silicon polymers, vinyl polymers, halogenated hydrocarbons, nylons, and proteinaceous materials, including copolymers or combinations thereof.

6. The composite according to claim 1 wherein the matrix is a thermoplastic polymer.

7. The composite of claim 1, wherein at least one of the first fibre type, the second fibre type, or the matrix is biodegradable.

8. The composite according to claim 1, wherein at least one of the first or second fibre types has a degradation rate which is faster than that of the matrix.

9. The composite according to claim 1, wherein the matrix has a faster rate of degradation than either the first or second fibre type or both.

10. The composite according to claim 1, further comprising additional fibres of one or more different type.

11. The composite according to claim 10, wherein the additional fibres are reinforcing fibres.

* * * * *